United States Patent

Suzuki

[11] 4,195,229
[45] Mar. 25, 1980

[54] X-RAY PHOTOGRAPHING APPARATUS

[75] Inventor: Tooru Suzuki, Atsugi, Japan

[73] Assignee: Tokyo Shibaura Electric Co., Ltd., Kawasaki, Japan

[21] Appl. No.: 865,869

[22] Filed: Dec. 30, 1977

[30] Foreign Application Priority Data

Jan. 5, 1977 [JP] Japan .................................. 52/149

[51] Int. Cl.² .................... G01N 21/34; G01N 23/04
[52] U.S. Cl. ................... 250/445 T; 250/505; 250/514; 250/354
[58] Field of Search .............. 250/445 T, 503, 505, 250/514, 354, 355

[56] References Cited

U.S. PATENT DOCUMENTS

| 4,005,311 | 1/1977 | Ledley | 250/445 T |
| 4,032,789 | 6/1977 | Workman | 250/445 T |
| 4,071,771 | 1/1978 | Covic et al. | 250/505 |

Primary Examiner—Craig E. Church
Assistant Examiner—Thomas P. O'Hare
Attorney, Agent, or Firm—Finnegan, Henderson, Farabow, Garrett & Dunner

[57] ABSTRACT

An X-ray photographing apparatus includes an X-ray tube for generating an X-ray pulse beam, a shutter for shutting off the X-ray pulse beam which is emitted from the X-ray tube, and a shutter controller for permitting the X-ray pulse beam shut off by the shutter to be passed therethrough when the intensity of the X-ray pulse beam from the X-ray tube reaches a substantially constant level. The apparatus permits the subject to be exposed at all times with a stabilized intensity of X-ray beam.

24 Claims, 8 Drawing Figures

F I G. 2
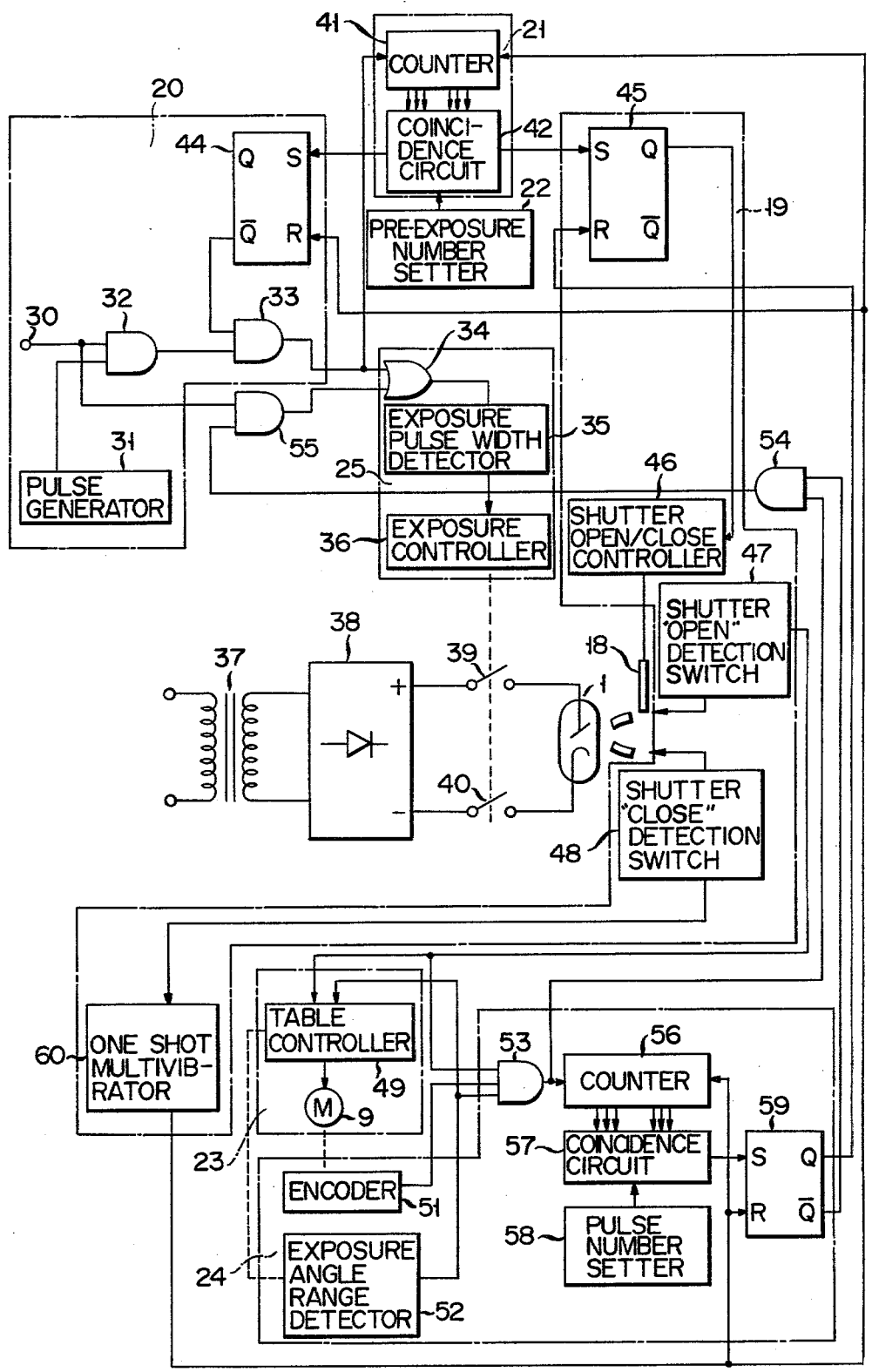

_4,195,229_

X-RAY PHOTOGRAPHING APPARATUS

BACKGROUND OF THE INVENTION

This invention relates to X-ray photographing apparatus and in particular to X-ray photographing apparatus including an X-ray shielding means.

As a prior art X-ray photographing apparatus a computed tomography is known which is adapted to expose a to-be-examined subject with an X-ray pulse beam, detect an X-ray beam portion penetrated through the subject, reconstitute the data of the detector by a computer and display as a tomographing image on a display the X-ray absorption coefficient of each part of the subject. There is also known a "cinecardioangiographing" apparatus (usually referred to as "cineangio") which is adapted to expose a subject with an X-ray pulse beam, after a contrast medium is injected into the blood vessel of the subject, and to photograph an X-ray pulse beam portion, by a cinecamera, which is penetrated through the subject.

In the above-mentioned X-ray photographing apparatus, pre-exposure is effected once a day before use to remove an initial X-ray output variation involved when X-ray exposure is started. When, however, the apparatus is repeatedly operated, such an initial X-ray output variation could not always be removed by a once-per-day pre-exposure. When pre-exposure is effected for each operation, a dissipation power is increased and a diagnosis processing capability is lowered. In this way, the conventional computed tomography requires a number of pre-exposures and it also requires a constant X-ray output. An initial X-ray output variation results in the degradation of a tomographing image on a display. Such initial X-ray output variation is removed in the conventional apparatus by detecting by means of a reference detector the intensity of X-ray pulse beam before its transmission through a subject, comparing the intensity of the X-ray beam before its transmission through the subject and the intensity of the X-ray beam after its transmission through the subject and removing some of the X-ray intensity variation. Since, however, two detectors used before and after the transmission of the X-ray beam through the subject, each, have a different characteristic, it is not sufficient in the conventional apparatus to completely remove an initial X-ray output variation.

SUMMARY OF THE INVENTION

It is accordingly the object of this invention to provide an X-ray photographing apparatus which can expose a to-be-examined subject at all times with a stable intensity of X-ray pulse beam.

According to this invention there is provided X-ray photographing apparatus comprising X-ray generating means for generating an X-ray pulse beam, X-ray shielding means for shutting off the X-ray pulse beam which is emitted from the X-ray generating means, and X-ray shielding means controlling means for permitting the X-ray beam shut off by the X-ray shielding means to be passed therethrough when the intensity of the X-ray pulse beam from the X-ray generating means reaches a substantially constant level.

BRIEF DESCRIPTION OF THE DRAWINGS

This invention will be further described by way of example by referring to the accompanying drawings, in which:

FIG. 2 is a block diagram showing in more detail a shutter control means of FIG. 1;

FIG. 4 is a graph showing a relation of the tube current through the X-ray tube to the number of X-ray exposures after a power supply is turned ON;

DETAILED DESCRIPTION OF THE PREFERRED EMBODIMENTS

An X-ray photographing apparatus of this invention as applied to X-ray photographing will now be explained below.

Figure 1:
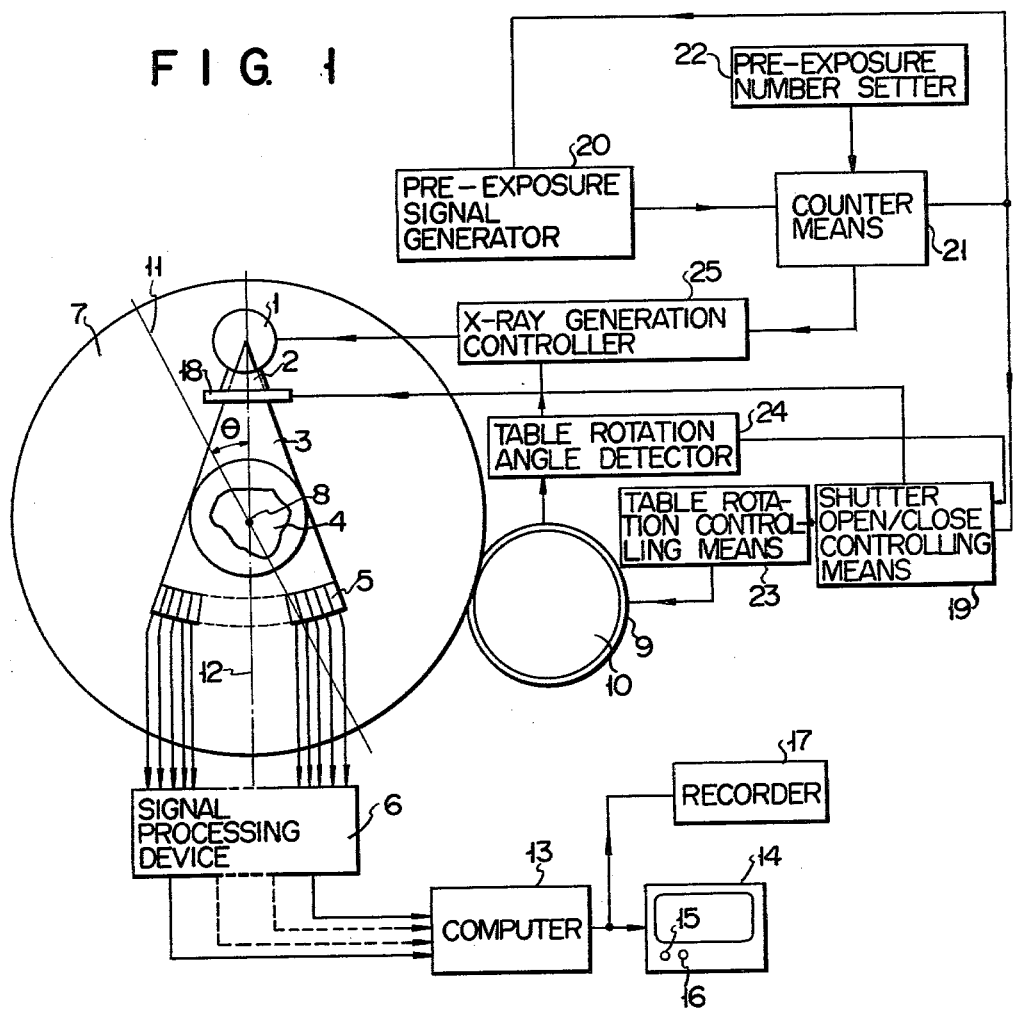
FIG. 1 is a schematic view showing a computed tomograph according to one embodiment of this invention.

As shown in FIG. 1 a fan-shaped X-ray beam 3 is emitted from an X-ray tube through a collimator 2 adjacent to the X-ray tube toward a to-be-examined subject 4 on the X-ray beam path to cause the subject to be exposed with an X-ray beam. The X-ray beam 3 is spread enough to cover the subject 4. The X-ray beam 3 is detected by a detector 5 disposed on the opposite side of the subject 4. As the detector use may be made of, for example, a detector utilizing the ionization of a high-pressure xenon gas sealed therein, a scintillation detector photomultiplier tube combination, or a semiconductor detector.

The output signal of the detector 5 is delivered to a signal processing device 6 where the intensity of the X-ray beam incident onto the subject 4 and the intensity of the X-ray beam penetrated through the subject 4 are quantitatively measured. The absorption coefficient of the subject 4 is calculated from such a ratio.

The X-ray tube 1 and detector 5 are supported by a table 7. The table 7 is rotated by a motor 9 with a central axis 8 as a center. The table 7 can be rotated by driving a drive gear 10, by means of the motor 9, which is in mesh with a gear (not shown) on the peripheral portion of the table 7. An angle θ made between the axis of the X-ray beam 3 and a phantom line 11 on the table 7 is varied in a range of 0° to 360°. Each time the angle θ takes predetermined values, the subject 4 is exposed with the X-ray beam, and that X-ray beam portion penetrated through the subject 4 is detected by the detector 5.

As already set out above, the output signal of the detector 5 is fed to the signal processing device 6 for the quantitative measurement of the intensity of the X-ray beam incident onto the subject 4 and the intensity of X-ray beam portion penetrated through the subject 4. The measured values are input to a computer 13 where they are computed and processed to obtain an absorption coefficient of each part of the subject 4. That is, the X-ray absorption coefficient of each part of the subject 4 is visually displayed by a display device such as a CRT.

The display device 14 has the function of photographing an image on its screen. A signal corresponding to the absorption coefficient of each part of the subject 4 is taken out with a certain width to represent a tomographing image on the screen of the display device. A pair of controllers 15, 16 are provided to control the absolute value of the absorption coefficient and the width of the coefficient. The output signal of the computer 13 is also supplied to a recorder 17 for recording. The recorder 17 may be of a type using a magnetic tape or a magnetic disk, or may be, for example, a line printer adapted to perforate a paper tape or a card for recording.

The X-ray beam emitted from the X-ray tube 1 passes through the collimator 2 to take a fan-shaped beam. A shutter 18 is disposed on one end of the collimator 2. The shutter is opened and closed by a shutter open/close controlling means 19. With the shutter closed the X-ray beam from the X-ray tube 1 is shut off. When the shutter 18 is opened the X-ray beam is directed to the subject 4 to permit the latter to be under exposure. Immediately after the X-ray tube is started, the shutter 18 is in the closed state. A shutter "open" control signal is sent to the shutter 18 by a shutter control means as will be explained below.

A "pre-exposure" signal is sent from a pre-exposure signal generator 20 through a counter means 21 and then through an X-ray generation controller 25 to the X-ray tube 1 and pre-exposure is effected with the shutter 18 closed. At this time, "pre-exposure" signals from the pre-exposure generator 20 are counted by the counter means 21. When the number of counts exceeds a preset value, the counter means 21 delivers a stop signal to the pre-exposure signal generator 20 to stop its "pre-exposure" signal. As a result, the pre-exposure is stopped. The preset value is set by a pre-exposure number setter 22. The stop signal of the counter means 21 is also supplied to the shutter open/close controlling means 19 to permit the shutter 18 to be opened.

The controlling means 19 delivers a signal to a table rotation controlling means 23. In consequence, the motor 9 is driven to cause the table 7 to be rotated through the drive gear 10. The rotation angle of the table 7 is detected by a table rotation angle detector 24 and the detection signal of the detector 24 is fed to the X-ray generation controller 25. The controller 25 delivers an exposure signal corresponding to each rotation angle of the table to the X-ray tube 1 and an X-ray beam is emitted from the X-ray tube according to the rotation angle of the table. In this way, exposure is effected. When a necessary number of exposures is effected to measure the distribution of the absorption coefficient of the subject, a signal is sent from the table rotation angle detector 24 to the shutter open/close controlling means 19 to cause the shutter 18 to be closed.

The shutter controlling means 19 will now be explained in more detail by referring to FIG. 2.

A start signal from a start pulse input terminal 30 in the pre-exposure signal generator 20 is supplied to one terminal of an AND gate 32. The output of the AND gate 32 is given the exposure conditions (pulse width, interval) by the output of the pulse generator 31, and it is delivered through an AND gate 33 and OR gate 34 to an exposure pulse width detector 35 adapted to prevent the subject from being exposed with an X-ray beam of a pulse width exceeding a preset pulse width. The exposure pulse width detector 35 consists of, for example, a monomultivibrator and an AND gate (not shown).

The output of the exposure pulse width detector 35 is fed to an exposure controller 36. High voltage switches 39 and 40 are closed by the output of the controller 36. As a result, a current flows through a transformer 37 and rectifier 38 and is fed as a DC current to the X-ray tube 1 to permit pre-exposure. At this time, pulses from a pulse generator 31 are fed through the AND gates 32 and 33 to a counter 41 where the number of pulses is counted. At this time, a flip-flop 44 is in the reset state and a "1" output signal is generated from the $\overline{Q}$ terminal of the flip-flop 44 and delivered to the AND gate 33. The number of "pre-expose" pulses is set beforehand by a pre-exposure number setter 22. A coincidence circuit 42, as part of the counter means 21, detects a coincidence between the count value of the counter 41 and the set value of the setter and sends a coincidence signal to the input terminal S of the flip-flop 44. A "0" output signal is then generated from the $\overline{Q}$ output terminal of the flip-flop 44 and it is fed to the AND gate 33. As a result, the pre-exposure is stopped.

During the pre-exposure period a "0" output signal is sent from the Q output terminal of a flip-flop 45 to a shutter open/close controller 46 to cause a shutter to be normally closed. When a signal is sent from the coincidence circuit 42 to the input terminal S of the flip-flop 45 a "1" output signal is generated from the Q output terminal of the flip-flop 45 and it is sent to the shutter controller 46 to cause the shutter to be opened.

The opening of the shutter 18 is detected by a shutter "open" detection switch 47 and a signal is delivered from the switch 47 to a table controller 49 constituting the table rotation controlling means 23, causing table rotation motor 9 to be started. The rotation angle of the table is detected by an encoder 51 for rotation angle detection. The encoder constitutes the table rotation angle detector 24. The encoder 51 generates a pulse signal (for example, a 300 pulse/per rotation signal) corresponding to the rotation angle of the table. An exposure angle range detector 52 generates a signal over an entire rotation range from a reference angle position where the table starts its rotation to the completion of the rotation of the table.

Signals from the switch 47, encoder 51 and detector 52 are fed through at an AND gate 53, the output of which is sent through an AND gate 54 and AND gate 55 to the OR gate 34 and follows the same route as in the case of pre-exposure. In this way, a regular exposure is effected. A "1" output signal is generated from the output terminal $\overline{Q}$ of a flip-flop 59 in the reset state and is supplied to the AND gate 54. The exposure is effected in synchronism with a pulse signal from the encoder 51. The width of the pulse signal is controlled by the exposure controller 36.

Signals from the AND gate 53 are counted by a counter 56. When the number of counts becomes equal to a pulse number (for example, 300 pulses) set in a pulse number setter 58, a coincidence signal is generated from a coincidence circuit 57 and delivered to the set terminal S of the flip-flop 59. As a result, a "1" output signal is generated from the $\overline{Q}$ output terminal of the flip-flop 59 and a "0" output signal is generated from the Q output terminal of the flip-flop 59. The "0" output signal disables the AND gate 54 to permit the X-ray exposure to be stopped. The "1" output signal from the Q output terminal of the flip-flop 59 resets the flip-flop 45 and a "0" output signal from the Q output terminal of the flip-flop 45 permits the shutter 18 to be closed. The closure of the shutter 18 is detected by a shutter "close"

detection switch 48. The detection signal is supplied to a one-shot multivibrator 60 where a narrow-width one-shot pulse is generated. The counters 41 and 56 and flip-flops 44 and 59 are reset by this pulse and the apparatus is returned to the original condition.

In this way, the X-ray exposure is effected and such an operation is completed for a brief time period such as 6 seconds.

Figure 3:
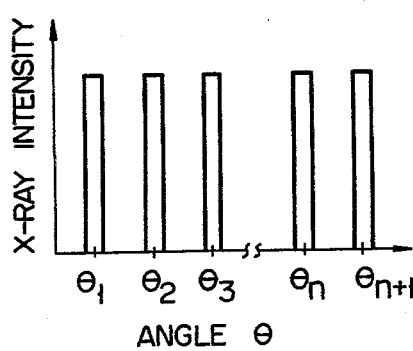
FIG. 3 is a graph showing a relation of an X-ray output of an X-ray tube to the rotation angle of a table.
Figure 4:
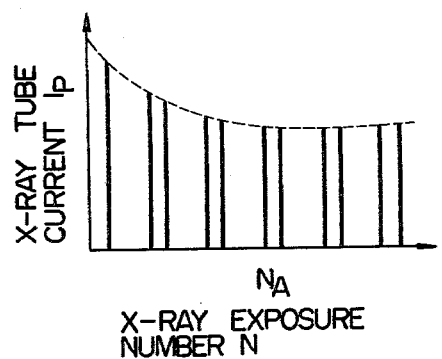

When the angle $\theta$ of FIG. 1 takes predetermined values $\theta_1, \theta_2 \ldots \theta_n$, an X-ray beam is emitted in the pulse-like form. This is shown in a graph of FIG. 3. FIG. 4 is a graph showing a relation of the current $I_P$ of the X-ray tube 1 to the number of exposures, N, made after the power source of the X-ray tube is turned ON. As will be apparent from the graph of FIG. 4 the tube current $I_P$ is monotonously decreased immediately after the turning ON of the power source, but it becomes substantially a constant level when a certain exposure number $N_A$ is reached. Such a phenomenon is due partly to the characteristic of the X-ray tube 1 and partly to, for example, the increase of an impedance resulting from a temperature rise in the filament circuit of the X-ray tube 1. Suppose that an exposure number $N_A$ at which the tube current $I_P$ is made constant is selected as a set value of the pre-exposure number setter 22. In this case, the fluctuation of the X-ray beam as involved immediately after the turning ON of the power source is shut off by the shutter 18. When the tube current $I_P$ reaches a constant level, the shutter is opened and the X-ray tube emits a constant output X-ray beam for exposure.

The forms of shutters for the X-ray photographing apparatus will now be explained below by referring to FIGS. 5 to 8.

An X-ray beam from the X-ray tube 1 is converted by the collimator 2 into a fan-shaped beam 3. The width of the fan-shaped beam 3 as measured at the outlet side of shutter 18 is determined by a slit 62 of a mask 61 provided on one side of the collimator 2 (see FIGS. 5 and 6). The width of the X-ray beam 3 can be varied by using a variety of masks having different slits. The shutter 18 is disposed ahead of the mask 61. As the material of the shutter 18, for example, lead can be used.

Figure 5:
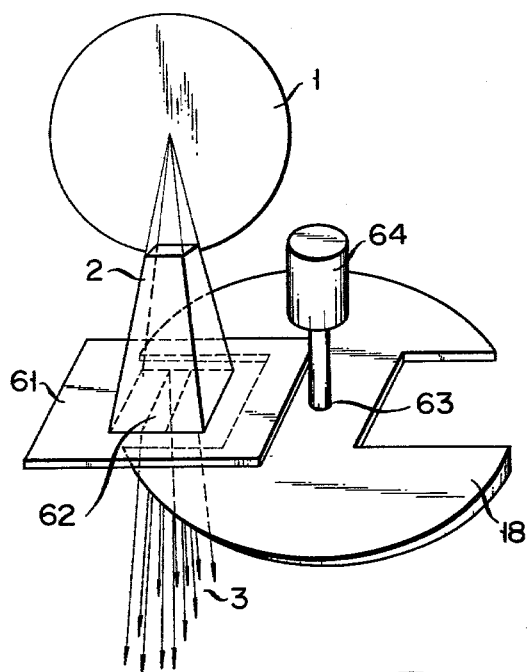
FIGS. 5 and 6 show one form of shutter mechanism of an X-ray photographing apparatus of this invention.
Figure 6:
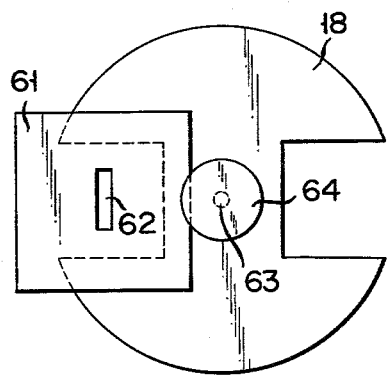

If, as the shutter, 18 use is made of a partially cut-off disk, an X-ray beam passes through the disk 18 when the slit 62 of the mask 61 aligns with the cut-off portion of the disk 18. When the slit 62 of the mask 61 confronts the uncut portion of the disk 18, the X-ray beam is shut off by the disk 18. The disk may have one or more cut-off portions. As shown in FIGS. 5 and 6, for example, a pair of opposite portions can be cut from the disk with a central point 63 as a center. When such disk shutter 18 is rotated with the central point 63 as a center, an X-ray beam is alternately passed through, and shut off by, the disk shutter 18 at a 90° step. A motor 64 has a drive shaft at the center of the shutter 18 and is driven by the shutter open/close controlling means 19. The opening and closing of the shutter 18 can be rapidly effected by such a shutter drive method.

Figure 7:
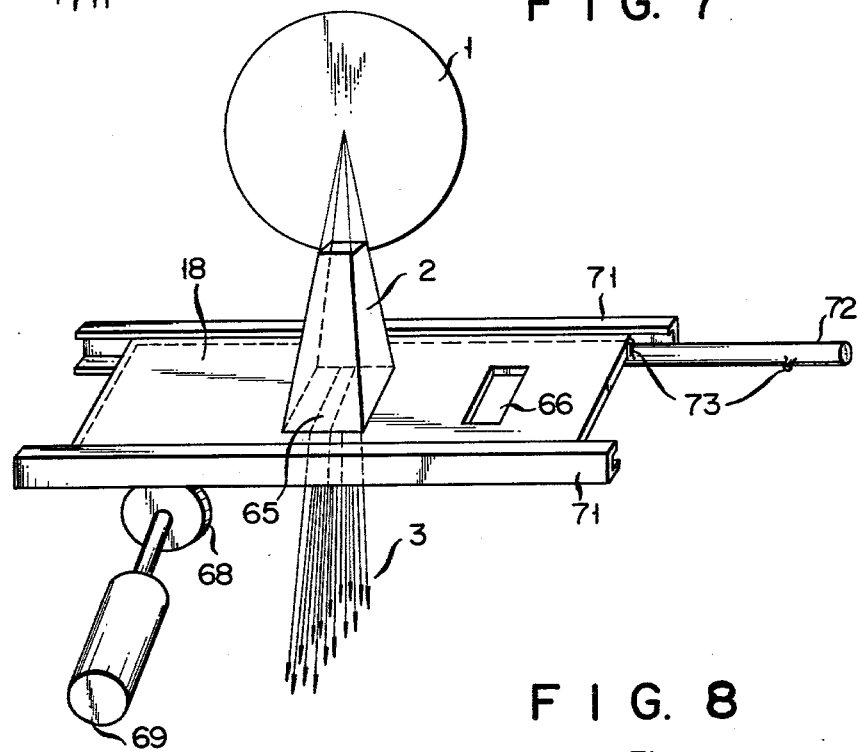
FIGS. 7 and 8 show another form of shutter mechanism of the X-ray photographing apparatus of this invention.
Figure 8:
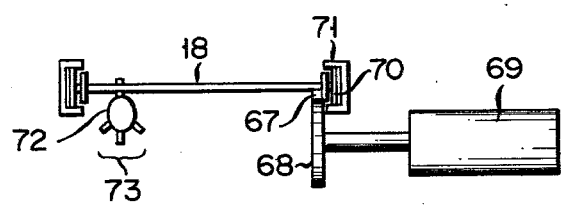

FIGS. 7 and 8 show another form of shutter. The shutter 18 of FIG. 7 has the double function of shutting off an X-ray beam (normal shutter function) and serving as a slit for determining the width of the X-ray. The shutter 18 of FIGS. 7 and 8 includes two slits 65 and 66 having different widths. When the slit 65 or 66 of the shutter aligns with the end of the collimator 2, an X-ray beam passes through the shutter 18. When the end of the collimator 2 faces an unslitted portion of the shutter 18 an X-ray beam is shut off by the shutter 18.

A rack 67 is provided on the undersurface of one end of the shutter 18. The shutter 18 is driven by a motor 69 through the rack 67 which is in mesh with a pinion 68. The drive of the motor 69 is controlled by the shutter open/close controlling means 19. Rollers 70 are provided at the sides of the shutter 18 and in a direction in which the shutter 18 is moved. The rollers 70 are rolled in a roller bearing 71 to permit the shutter 18 to be smoothly driven.

A shutter stop mechanism is provided on the shutter to stop the shutter in position. For example, a shutter stop mechanism 72 having projections 73 can be provided on the shutter 18 shown in FIG. 7. Alternatively, a microswitch may be provided in the roller bearing 71. In this case, the motor 69 is stopped when the shutter 18 passes through the microswitch. The shutter stop mechanism can be stopped through the shutter open/close controlling means 19.

As will be evident from the above, the X-ray photographing apparatus according to this invention can positively shut off an initial fluctuation of X-ray beam as occurring immediately after the power source is turned ON and direct a stabilized intensity of X-ray beam at all times toward the subject for exposure. When this invention is applied particularly to the computed tomography requiring a stabilized intensity of an X-ray beam, a tomographing image of the subject is much improved.

What we claim is:

1. An X-ray photographing apparatus comprising:
   X-ray generating means for generating an X-ray pulse beam;
   X-ray shielding means for shutting off the X-ray pulse beam emitted from said X-ray generating means;
   means for determining when the output intensity of the X-ray pulse beam from said X-ray generating means reaches a substantially constant level and for generating a pre-exposure termination signal;
   means for controlling said X-ray shielding means and for permitting it to be opened upon receipt of said pre-exposure termination signal; and
   an X-ray generation controller responsive to said determining means when the output intensity of the X-ray pulse beam from said X-ray generating means does not reach said substantially constant level to maintain said X-ray shielding means in said X-ray pulse beam path and responsive to said controlling means when the output intensity of the X-ray pulse beam reaches said substantially constant level to remove said X-ray shielding means from said X-ray pulse beam path.

2. An X-ray photographing apparatus according to claims 1, in which said determining means includes an X-ray pre-exposure signal generator, a pulse signal setter in which a predetermined number of pulse signals generated from said X-ray pre-exposure signal generator are set, and counter means for counting the number of pulse signals, said X-ray generation controller being adapted to be operated by the pulse signal from said X-ray pre-exposure signal generator when the count number of said counter means does not reach said predetermined number of said setter and adapted to be operated by a signal from said controlling means when the count number of said counter means reaches said predetermined number of said setter.

3. An X-ray photographing according to claim 2, in which said X-ray shielding controlling means comprises a flip-flop connected to said counter means, an X-ray shielding means open/close controller for controlling the opening and closing of said X-ray shielding means in response to the output signal of the flip-flop, a first detection switch for detecting an open state of said X-ray shielding means, a second detection switch for detecting a closed state of said X-ray shielding means, and a one-shot multivibrator driven by a detection signal from said second detection switch.

4. An X-ray photographing apparatus according to claim 1, in which said X-ray shielding means comprises a collimator for permitting the X-ray pulse beam emitted from said X-ray generating means to be converted into a fan-shaped beam, a slitted mask for determining the width of the X-ray beam, a shutter for permitting the passage or shut off of the X-ray beam, and a driving means for driving the shutter.

5. An X-ray photographing apparatus according to claim 2, in which said X-ray shielding means comprises a collimator for permitting the X-ray pulse beam emitted from said X-ray generating means to be converted into a fan-shaped beam, a slitted mask for determining the width of the X-ray beam, a shutter for permitting the passage or shut-off of the X-ray beam, and a driving means for driving the shutter.

6. An X-ray photographing apparatus according to claim 4, in which said shutter is formed of a plate member having at least one cut-off portion, in which when the X-ray beam aligns with the cut-off portion of said plate member the X-ray passes therethrough and when the X-ray beam faces the non-cut portion of said plate member the X-ray beam is shut off.

7. An X-ray photographing apparatus according to claim 5, in which said shutter is formed of a plate member having at least one cut-off portion, in which when the X-ray beam aligns with the cut-off portion of said plate member the X-ray passes therethrough and when the X-ray beam faces the non-cut portion of said plate member the X-ray beam is shut off.

8. An X-ray photographing apparatus according to claim 6, in which said shutter is intermittently driven by the driving means to cause the passage and shut off of the X-ray to be alternately effected.

9. An X-ray photographing apparatus according to claim 7, in which said shutter is intermittently driven by the driving means to cause the passage and shut off of the X-ray to be alternately effected.

10. An X-ray photographing apparatus according to claim 1, in which said X-ray shielding means comprises a collimator for permitting the X-ray beam emitted from the X-ray generating means to be converted into a fan-shaped beam, a shutter member having at least one slit for determining the width of the X-ray beam, the X-ray beam being shut off by the unslitted portion of the shutter member, a drive mechanism for driving said shutter member, and a position setting mechanism for determining the position of the shutter member.

11. An X-ray photographing apparatus according to claim 2, in which said X-ray shielding means comprises a collimator for permitting the X-ray beam emitted from the X-ray generating means to be converted into a fan-shaped beam, a shutter member having at least one slit for determining the width of the X-ray beam, the X-ray beam being shut off by the unslitted portion of the shutter member, a drive mechanism for driving said shutter member, and a position setting mechanism for determining the position of the shutter member.

12. An X-ray photographing apparatus according to claim 10, in which said shutter member includes at least two slits having different widths, through which a corresponding width of X-ray beam passes.

13. An X-ray photographing apparatus according to claim 11, in which said shutter member includes at least two slits having different widths, through which a corresponding width of X-ray beam passes.

14. An X-ray photographing apparatus according to claim 10, in which said drive mechanism comprises a rack provided on the shutter member, a pinion mounted to engage with the rack, a motor for rotating the pinion, a roller mounted on the shutter member to permit smooth movement of the shutter, and a roller bearing.

15. An X-ray photographing apparatus according to claim 12, in which said drive mechanism comprises a rack provided on the shutter member, a pinion mounted to engage with the rack, a motor for rotating the pinion, a roller mounted on the shutter member to permit smooth movement of the shutter, and a roller bearing.

16. An X-ray photographing apparatus according to claim 10, in which said position setting apparatus is constructed of a shutter stop mechanism having a plurality of projections for stopping the movement of the shutter member when the axis of the X-ray beam is brought substantially into alignment with the center of the slit of the shutter member.

17. An X-ray photographing apparatus according to claim 12, in which said position setting apparatus is constructed of a shutter stop mechanism having a plurality of projections for stopping the movement of the shutter member when the axis of the X-ray beam is brought substantially into alignment with the center of the slit of the shutter member.

18. An X-ray photographing apparatus according to claim 14, in which said position setting apparatus is constructed of a shutter stop mechanism having a plurality of projections for stopping the movement of the shutter member when the axis of the X-ray beam is brought substantially into alignment with the center of the slit of the shutter member.

19. An X-ray photographing apparatus according to claim 1, further comprising detector means for detecting that X-ray beam portion penetrated through a to-be-examined subject to which X-ray beam is initially emitted from said X-ray generating means, computer means for effecting calculation upon receipt of a signal from said detector means so as to obtain a tomographing image of the subject, and display means for displaying said tomographing image based on the calculation of said computer means.

20. An X-ray photographing apparatus according to claim 2, further comprising detector means for detecting that X-ray beam portion penetrated through a to-be-examined subject which X-ray beam is initially emitted from said X-ray generating means, computer means for effecting calculation upon receipt of a signal from said detector means so as to obtain a tomographing image of the subject, and display means for displaying said tomographing image based on the calculation of said computer means.

21. A computed tomographic system comprising:
means for generating an X-ray pulse beam;
means for detecting the portion of said X-ray beam penetrating through the subject to be examined;
computer means for reconstituting data received from said detecting means to obtain a tomographing image of the subject;

means for displaying said tomographing image;

X-ray shielding means for shutting off the X-ray pulse beam emitted from said X-ray generating means;

means for determining when the output intensity of the X-ray pulse beam from said X-ray generating means reaches a substantially constant level and for generating a pre-exposure termination signal;

means for controlling said X-ray shielding means and for permitting it to be opened upon receipt of said pre-exposure termination signal; and an X-ray generation controller responsive to said determining means when the output intensity of the X-ray pulse beam from said X-ray generating means does not reach said substantially constant level to maintain said X-ray shielding means in said X-ray pulse beam path and responsive to said controlling means when the output intensity of the X-ray pulse beam reaches said substantially constant level to remove said X-ray shielding means from said X-ray pulse beam path.

22. A computed tomographic system according to claim 21, in which said determining means includes an X-ray pre-exposure signal generator, a pulse signal setter in which a predetermined number of pulse signals generated from said X-ray pre-exposure signal generator are set, and counter means for counting the number of pulse signals, said X-ray generation controller being adapted to be operated by the pulse signal from said X-ray pre-exposure signal generator when the count number of said counter means does not reach said predetermined number of said setter and adapted to be operated by a signal from said controlling means when the count number of said counter means reaches said predetermined number of said setter.

23. The computed tomographic system of claim 21 also including means for recording the data reconstituted by said computer means.

24. The computed tomographic system of claim 22 also including means for recording the data reconstituted by said computer means.

* * * * *